United States Patent [19]

Lewis et al.

[11] 4,450,099

[45] May 22, 1984

[54] BARIUM HYDRIDE MODIFIED ALUMINUM/SILICEOUS COMPOSITIONS

[75] Inventors: Robert M. Lewis, Sugarland; Lynn H. Slaugh, Cypress, both of Tex.

[73] Assignee: Shell Oil Company, Houston, Tex.

[21] Appl. No.: 477,182

[22] Filed: Mar. 21, 1983

[51] Int. Cl.³ .................. B01J 21/08; B01J 29/00; B01J 21/10; B01J 23/08

[52] U.S. Cl. .................. 502/232; 502/240; 502/250; 502/341

[58] Field of Search ............ 252/451, 455 R; 502/341, 250

[56] References Cited

U.S. PATENT DOCUMENTS

| | | | |
|---|---|---|---|
| 2,188,007 | 1/1942 | Kistler | 252/451 X |
| 2,281,919 | 5/1942 | Connolly | 252/451 X |
| 2,680,100 | 1/1954 | Elston | 252/451 |
| 2,699,430 | 1/1955 | Teter | 252/451 X |
| 2,731,452 | 1/1956 | Field et al. | 252/458 X |
| 2,852,576 | 9/1958 | Fotis et al. | 252/455 R |
| 2,900,349 | 8/1959 | Schwartz | 252/451 X |
| 2,935,483 | 5/1960 | Schwartz | 252/455 R |
| 2,958,648 | 11/1960 | Broithwaite | 252/455 R X |
| 3,526,601 | 9/1970 | Fotis, Jr. et al. | 252/465 X |
| 3,893,943 | 7/1975 | Willard, Sr. | 252/451 X |
| 4,235,756 | 11/1980 | Slaugh | 252/463 |
| 4,239,872 | 12/1980 | Slaugh | 252/464 X |
| 4,295,999 | 10/1981 | Slaugh | 252/458 X |
| 4,367,361 | 1/1983 | Slaugh | 585/532 X |
| 4,368,342 | 1/1983 | Slaugh | 585/457 X |
| 4,375,574 | 3/1983 | Slaugh | 585/474 |
| 4,375,575 | 3/1983 | Slaugh | 585/481 X |
| 4,384,154 | 5/1983 | Slaugh | 585/415 |

*Primary Examiner*—Delbert E. Gantz
*Assistant Examiner*—William G. Wright

[57] ABSTRACT

Novel compositions are prepared by reacting barium hydride and metal oxide gels in the slurry phase. These compositions are useful as catalysts and catalyst supports.

8 Claims, 1 Drawing Figure

BARIUM HYDRIDE MODIFIED ALUMINUM/SILICEOUS COMPOSITIONS

FIELD OF THE INVENTION

This invention relates to novel aluminous, aluminosiliceous, and siliceous compositions modified with barium hydride. These compositions are useful as catalysts and catalyst supports, particularly as supports for syngas catalysts.

BACKGROUND OF THE INVENTION

Aluminas, silicas and alumino-silicas find frequent use as catalysts and as supports for catalyst metals. The support itself can in many instances modify the catalyzed reaction. Modifications of the support can thus effect the catalyst activity and selectivity as well as change the product mix. Various means have been utilized to add modifiers to supports. A frequently used method is to impregnate the support with dissolved salt or compound and then calcine the impregnated material.

In Russian Inventors' Certificate No. 584,886, there is disclosed the preparation of supported niobium hydride catalysts. In this reference, however, the hydride is not reacted with the support but exists as the unreacted hydride on the support.

In U.S. Pat. No. 3,146,209 issued Aug. 25, 1964, a solution of etherated aluminum hydride is used to react with a metal oxide gel substrate.

In U.S. Pat. No. 4,235,756 issued Nov. 25, 1980 and in U.S. Pat. No. 4,335,022 issued June 15, 1982 a solution of aluminum hydride is used to impregnate an alumina gel or a silica gel which is subsequently calcined.

SUMMARY OF THE INVENTION

This invention relates to novel metal oxide gel compositions. These compositions have been modified with barium hydride and fine use as catalysts and as catalyst supports. In general, they are prepared by contacting a substantially anhydrous metal oxide gel with a powdered barium hydride in the slurry phase wherein the slurrying medium is an anhydrous, non-hydroxyl-containing organic liquid wherein preferably the amount of barium hydride utilized is not greater than the amount needed to completely react with hydroxyl moieties present in the metal oxide gel. After contact and reaction with the hydride, the metal oxide gel is dried to remove the solvent and optionally calcined at elevated temperatures. When these barium hydride modified compositions are used to prepare ruthenium-containing syngas catalysts for the conversion of syngas to olefins, it has been found that the barium modified compositions minimize olefin isomerization.

BRIEF DESCRIPTION OF THE DRAWING

The sole drawing illustrates the use of the instant compositions as catalyst supports for ruthenium catalyzed syngas reactions. Curve A uses barium-modified silica compositions of the instant invention. Curve B uses pure silica.

DESCRIPTION OF THE PREFERRED EMBODIMENT

Figure 1:
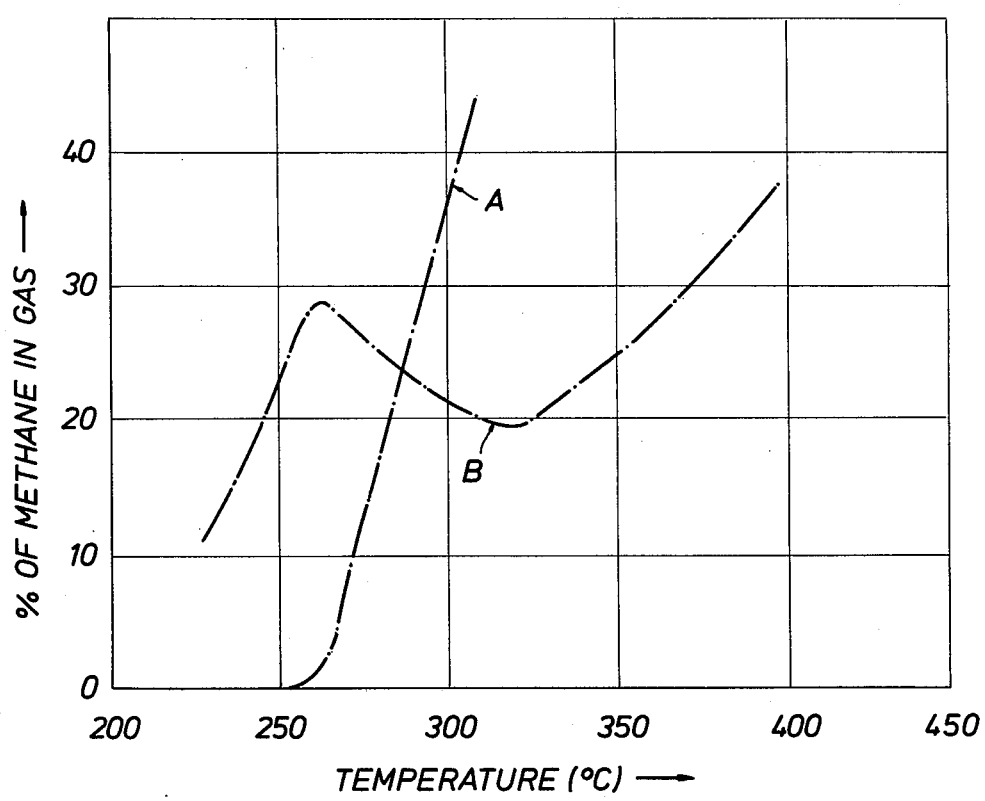

The gel oxides suitable for use in preparing the compositions of the instant inventions are any of the metal oxide gels that are well known in the catalytic art useful as either catalyst base materials or as promoting materials in catalyst compositions. Additionally, the term "metal oxide gel" as used herein shall also include the plural oxide gels, i.e., those that contain mixtures or compounds of two or more metal oxides. A metal oxide gel is basically a metal oxide that contains chemically bound water in the form of hydroxyl groups. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the composition of this invention are aluminas, silicas, alumina-silicas, alumina-zirconias, silica-zirconias and the like, including naturally occurring hydrous oxide minerals such as clays. Preferred oxide gel materials are selected from the group consisting of alumina, silica and alumina-silica.

Prior to use the metal oxide gels should be substantially free of absorbed water, i.e., "substantially dehydrated or anhydrous". The absorbed or free water is removed by heating the gels at temperatures ranging from about 100° C. to about 900° C. prior to contact with the hydride. Any environment that provides for drying is suitable such as air, vacuum, inert gas such as nitrogen, etc. The dried gels should be kept away from a humid atmosphere after drying. It is understood that a dried gel will still contain chemically bound water in the form of hydroxide and hydroxyoxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a cogel. In fact "impurities" may be purposely added for catalytic effects. The following table lists several commercial aluminas and their properties which are found suitable.

| Alumina | Surface Area $m^2$g | Pore Vol., cc/gm | Na, ppm | $SO_4^=$, % wt | $Fe_2O_3$ % wt | $Cl^-$ % wt |
|---|---|---|---|---|---|---|
| CCI[a] | 252 | 0.8 | 160 | 0.06 | — | 0.02 |
| KA-209[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 0.51 | 0.03 | — | 0.03 |

[a]Catalysts & Chemicals, Inc., now United Catalysts
[b]Kaiser
[c]Reynolds Corp.
[d]American Cyanamid Corp.
[e]Conoco Corp.
[f]Filtrol Corp.

Silica gel is also another preferred substrate. These are readily available commercially and are essentially substantially dehydrated amorphous silica. These materials are available in various density grades, from low density with surface areas ranging from about 100–200 $m^2$/g to regular density with surface areas up to about 800 $m^2$/g. The commercially available materials are used as dessicants, selective absorbents, catalysts and catalyst supports. Regarding purity of the silica, it may be stated that small amounts of impurities are not generally detrimental and may be beneficial when the impurity is present as a co-gel. In fact, "impurities" may be purposely added for catalytic effects. The following table lists several commercial silicas and their properties which are found suitable.

| Support | Surface Area, m²/g | Pure Vol, cc/g | Density g/cc | Particle Size |
|---|---|---|---|---|
| Davison* Grade 952 $SiO_2$ | 300 | 1.65 | 0.35 | 70 mesh (avg) |
| Davison Grade 57 $SiO_2$ | 300 | 1.0 | 0.4 | 100 mesh |
| Davison Grade 03 $SiO_2$ | 750 | 0.43 | 0.7 | 8 mesh (avg) |

*Manufactured by Davison Chemical Div., W. R. Grace & Co.

Other preferred substrates are the alumino-silicates. These materials contain various mixtures of aluminum and silicon oxides. They are readily available commercially and are generally employed as cracking catalysts. Typically they contain from about 50 to about 95, preferably from about 70 to about 90 percent by weight of silica. Illustrations of commercially available alumina-silicas are Davison Grade 980-25 (manufactured by Davison Chemical Division, W. R. Grace & Co.) which contains about 75% $SiO_2$ and 25% $Al_2O_3$ and Davison Grade 980-13 which contains about 87% $SiO_2$ and 13% $Al_2O_3$. These materials can be prepared in a conventional fashion, as for example by co-precipitation, co-gellation, or by spray drying.

In general, the compositions of the instant invention are prepared by contacting the substrate with barium hydride in a slurry phase and allowing the hydride to react with the substrate, which reaction is evidenced by the evolution of hydrogen gas. The temperature of contact is not critical and is generally made at room temperature, although higher or lower temperatures are not precluded. In general contact temperatures of about 0°–100° C. are utilized. After reaction, this barium is present in and on the metal oxide gel in the form of an oxide or oxygen-containing compound of barium complexed with the metal oxide(s) of the gel, although the exact form of the barium oxide is not known.

The barium hydride used to prepare the slurry is prepared commercially by the direct reaction of the metal and hydrogen at 300° C. The reaction is highly exothermic and goes to completion rapidly. To prepare the slurry, the barium hydride is ground to a fine powder, for example, less than 60, preferably less than 100 mesh and then mixed with an anhydrous, non-hydroxyl containing organic solvent. Both water and hydroxylic materials react with the barium hydride and therefore during the processing of the compositions of the instant invention, contact with water, and other hydroxyl-containing materials should be avoided. However, once the compositions are prepared by reaction with the barium hydride, they are no longer sensitive to water or other hydroxyl-containing materials. The inert solvent used to prepare the slurry of barium hydride should be a solvent that is inert to barium hydride. Suitable solvents include alkanes such as hexane, cyclohexane, heptane, dodecane, etc., ethers, such as dimethyl ether, diethyl ether, tetrahydrofuran, etc., and ketones such as dimethyl ketone, methyl isobutyl ketone, methylethyl ketone, etc.

In general, an amount of barium hydride is used to react with the substrate in an amount that does exceed that amount that is needed to completely react with the hydroxyl moieties present in the metal oxide gel substrate, i.e., an excess of hydride is not used, although lesser amounts than necessary to completely react with the substrate are frequently used. If amounts of barium hydride greater than that needed to completely react with the hydroxyl moieties present in the substrate are utilized, then upon completion of the reaction, excess barium hydride would be left in the substrate. This "free" barium hydride would be converted to barium oxide or hydroxide upon contact with hydroxyl-containing materials or by calcination in air at elevated temperatures, but would be in a different form from the barium oxide prepared by reaction of the hydride with the substrate. Thus, the use of excess barium hydride would provide a composition according to the instant invention which would also contain "free" (i.e., unreacted with the substrate) barium hydride, hydroxide or oxide. In general, the composition of the instant invention will contain from about 0.001 to about 50, preferably from about 0.01 to about 25 and more preferably from about 0.1 to about 10 percent by weight of barium measured in the metal.

In a preferred embodiment, the instant compositions are prepared by adding powdered barium hydride to a slurry of metal oxide gel particles under dry box conditions. Alternatively, the metal oxide gel particles can be added to a slurry of barium hydride powder. The resultant mixture is stirred until reaction has ceased as indicated by the cessation of hydrogen evolution. After reaction, the compositions are filtered and dried to remove the solvent. Optionally, the compositions are frequently calcined at temperatures ranging from about 200° C. to 900° C. prior to use as catalysts or catalyst supports.

The compositions of the instant invention can be utilized as catalysts and as catalyst supports. The barium modified materials have different physical and chemical properties than the unmodified materials or materials modified using other compounds. For example, the instant compositions have physical characteristics and properties that differ from those materials prepared, for example, by impregnating substrates with barium nitrate and calcining.

To illustrate the different physical characteristics, a composition of the instant invention comprising barium/silica and a comparative composition prepared by impregnating silica gel with an aqueous solution of barium nitrate and subsequently calcining, were analyzed using X-ray photoelectron spectroscopy (XPS). The samples were prepared for analyses by grinding in an argon atmosphere, followed by mounting on polymer tape. The XPS spectra were recorded in a Varian IEE spectrometer. The relative number of atoms seen on the surface of the compositions using X-ray photoelectron spectroscopy was determined from the core level spectra for the 3d and 4d levels of barium, the 2p level of silica and the 1s level of oxygen and are shown in Table I.

TABLE I

| Element and Core Level | from $BaH_2$/Silica gel | from $Ba(NO_3)_2$/Silica gel |
|---|---|---|
| Ba 3d | 8.6 | 2.6 |
| Ba 4d | 5.5 | 1.6 |
| Si 2p | 62 | 57 |
| O 1s | 167 | 161 |

As can be seen from Table 1, the compositions according to this invention have the barium distributed over the surface in a significantly different manner than the conventionally prepared barium nitrate impregnated material.

The compositions of the instant invention and their use as catalysts will be further described below by the following illustrative embodiments which are provided for illustration and are not to be construed as limiting the invention.

ILLUSTRATIVE EMBODIMENTS

Composition Preparation

The following example illustrates the preparation of compositions according to the instant invention.

In a dry box, barium hydride powder (0.5 g; less than about 100 mesh) was added with stirring to a slurry of calcined Kaiser KA 201 Alumina (9.5 g, 20–30 mesh) in dry tetrahydrofuran (20 ml). Stirring was continued for a period of 2 days in a sealed vessel. At the end of the 2 day period the flask was opened and the tetrahydrofuran was allowed to evaporate. The resultant composition contained about 5.3% wt barium measured as the metal.

A similar composition was prepared using the technique described above and Davison Grade 57 Silica.

As can be seen from the FIGURE the compositions of the instant invention when used as supports provide different catalytic responses as a function of temperature than do unmodified silica.

The products formed by the above reactions were analyzed for paraffins and olefins by gas chromatography to provide a relatively quantitative measure of olefin isomerization. An isomerization equivalent is determined from the GC results. This involves the ratio of paraffin to olefin peak heights. As more isomerization occurs, the peak height ratio increases. This needs to be corrected, however, for the relative amounts of the olefins compared to the paraffins. This can be done by multiplying the paraffin to olefin peak height ratio by the olefin to paraffin peak area ratio. This method does not take into account the relative response factors, peak half widths, etc. However, with no isomerization occurring, the isomerization equivalent should be near one. With isomerization occurring, the number should be greater than one. The isomerization equivalents calculated for the various catalysts are tabulated in Table 1. These numbers demonstrate the remarkable effect the barium has on stopping the olefin isomerization.

TABLE 1

| Catalyst (8.9% Ru on $SiO_2$) | Paraffin/Olefin Peak Height* | | Olefin/Paraffin Peak Area* | | Isomerization Equivalent | |
|---|---|---|---|---|---|---|
| | ~250° C. | ~300° C. | ~250° C. | ~300° C. | ~250° C. | ~300° C. |
| No Metal Hydride | 1.05 | 0.69 | 1.97 | 2.01 | 2.1 | 1.4 |
| 20% $BaH_2$ | 0.33 | 0.53 | 1.93 | 1.85 | 0.6 | 1.0 |

*Based on g.c. data for $C_{14}$ fraction.

Utilization of Composition as Catalyst Support

A sample of a barium-modified silica composition (20% wt Ba) prepared as described above was dried under high vacuum and pelletized to 20-30 mesh size. The composition (5.7 g, 9 ml) was impregnated with a solution of ruthenium trichloride in water (1.04 g of $RuCl_3.XH_2O$ in 7 ml deionized water). This gave about 8.9% weight ruthenium on the support.

The impregnated support was calcined in a quartz tube by heating to 250° C. under nitrogen gas flow (500 cc/min) for 4 hours.

The calcined catalyst was transferred to a 1.4 cm ID hih-pressure 316 stainless steel tubular reactor. Silicon carbide chips (18 ml each) were used above and below the catalyst to support it in the center of the reactor.

The catalyst was reduced by hydrogen at 900 psig and a flow of 500 cc/min. by heating the reactor over a 2 hour period to 450° C. and holding at 450° C. for an additional 2 hour period.

The reactor was allowed to cool to room temperature and carbon monoxide and hydrogen in a 1:1 molar ratio was passed over the catalyst at 500 cc/min (GHSV about 3000). The reactor was then heated to the desired temperature. The weight of methane in the product was determined and and is plotted in the FIGURE as Curve A as a function of temperature.

The above was repeated using as a support untreated Davison Grade 57 Silica. The results are shown as Curve B in the FIGURE.

We claim:

1. A process for preparing a metal oxide gel composition having bonded thereto barium oxide, which process comprises contacting a substantially anhydrous metal oxide gel with a powdered barium hydride in a slurry phase with the slurrying medium being an anhydrous, non-hydroxyl-containing organic liquid whereby the barium hydride reacts with the metal oxide gel, and subsequently drying the gel to remove the organic liquid.

2. The process of claim 1 wherein the metal oxide gel is selected from the group consisting of aluminum oxide gel, silicon oxide gel and aluminum-silicon oxide gel.

3. The process of claims 1 or 2 wherein the amount of barium hydride utilized is not greater than the amount needed to completely react with hydroxyl moieties present in the metal oxide gel.

4. The process of claims 1 or 2 wherein the slurrying liquid is tetrahydrofuran.

5. The process of claims 1 or 2 wherein the magnesium hydride powder is less than about 100 mesh in size.

6. The process of claims 1 or 2 wherein, after drying, the gel is calcined at a temperature ranging from about 200° C. to about 900° C.

7. The process of claims 1 or 2 wherein the barium in the composition ranges from about 0.001 to about 50 percent by weight measured as barium metal.

8. The process of claims 1 or 2 wherein the barium in the composition ranges from about 0.01 to and 25 percent by weight measured as barium metal.

* * * * *